(12) United States Patent
Haytman et al.

(10) Patent No.: US 6,511,434 B1
(45) Date of Patent: Jan. 28, 2003

(54) BLOOD-PRESSURE TRANSDUCER ASSEMBLY

(75) Inventors: Eyal Haytman, Merom Hagalil (IL); Gilles Fitoussi, Merom Hagalil (IL); David Ziv, Merom Hagalil (IL)

(73) Assignee: Elcam Plastic Cooperative Agricultural Association Ltd., Merom Hagalil (IL)

( * ) Notice: Subject to any disclaimer, the term of this patent is extended or adjusted under 35 U.S.C. 154(b) by 0 days.

(21) Appl. No.: 09/876,850

(22) Filed: Jun. 7, 2001

(51) Int. Cl.[7] .................................................. A61B 5/02
(52) U.S. Cl. ........................................ 600/488; 600/479
(58) Field of Search ............................. 600/5, 300, 485, 600/486, 488, 493, 494, 490, 503; 604/505; 128/DIG. 13

(56) References Cited

U.S. PATENT DOCUMENTS

| | | | |
|---|---|---|---|
| 3,675,891 A | 7/1972 | Reynolds et al. | 251/117 |
| 4,291,702 A | 9/1981 | Cole et al. | 128/675 |
| 4,464,179 A | 8/1984 | Barger et al. | 604/250 |
| 4,545,389 A | 10/1985 | Schaberg et al. | 128/748 |
| 4,825,876 A * | 5/1989 | Beard | 600/488 |
| 4,934,375 A | 6/1990 | Cole et al. | 128/673 |
| 5,649,542 A * | 7/1997 | Archibald et al. | 600/485 |
| 6,052,613 A * | 4/2000 | Takaki | 600/479 |

* cited by examiner

*Primary Examiner*—Tu Ba Hoang
(74) *Attorney, Agent, or Firm*—Ladas & Parry

(57) ABSTRACT

A unitary blood-pressure transducer assembly for inclusion in a system adapted to monitor the blood pressure of a patient while the patient is being supplied through a supply line leading to a catheter implanted in a blood vessel with a saline liquid. The assembly includes free sub-assemblies housed within a common casing and having an inlet port to be coupled to the upstream section of the line and an outlet port to be coupled to the downstream section whereby the liquid flows through the assembly. Intermediate the ports is a first sub-assembly having a transducer that senses the pressure of a column of liquid developed within the assembly, whose pressure varies as a function of the pressure of the blood streaming through the blood vessel. Adjacent the inlet port is a second sub-assembly that includes a fast-flush valve to purge air bubbles from the assembly and a flow restrictor to maintain liquid flow at a low flow rate. The third sub-assembly which is adjacent the outlet port includes a stopcock to selectively direct flow to allow for priming and zeroing of the system as well as blood sampling.

11 Claims, 4 Drawing Sheets

BLOOD-PRESSURE TRANSDUCER ASSEMBLY

BACKGROUND OF THE INVENTION

1 Field of the Invention

This invention relates generally to systems for monitoring the blood pressure of a patient, and more particularly, to an integrated, blood-pressure transducer assembly for inclusion in such systems.

2 Status of Prior Art

It is common practice to provide in a hospital or other facility in which a patient is being treated, a system adapted to continuously measure and monitor the patient's blood pressure. In a typical system of this type, the pressure exerted on a column of liquid that communicates with the patient's blood stream via a catheter implanted in an artery or vein of the patient is sensed by a pressure-sensitive transducer which generates an electrical signal that varies as a function of blood pressure. This signal is conveyed to a monitor on whose screen is displayed He waveform of the signal. And the signal may also be recorded on a print chart to provide a record of the changing blood pressure of the patient in the course of a hospital stay.

The liquid column is derived from an IV bag supported at an elevated position adjacent the patient, the bag containing a saline liquid gravity fed by a supply line to the catheter from which it enters the blood stream. Hence the pressure of the blood is exerted on the liquid column. In practice, a pressurized source of a saline or other liquid may be used, in which event there is no need to elevate the bag.

It is essential hat the liquid flow continuously at a low drip raze in order to keep open the supply line and the catheter. Should the end of the catheter become occluded because of a blood clot or thrombosis, the system would then produce an erroneous blood-pressure reading. The reason therefore that it is vital to maintain a continuous flow of the saline solution through the catheter is in order to avoid the formation of blood clots. Also it is vital that the system be purged of air bubbles.

Air bubbles are compressible and therefore give rise to an uncertain pressure differential between the patient's blood stream and the pressure transducer, thereby resulting in a measurement error. Moreover, one cannot tolerate the entry of air bubbles into the blood steam, for his may have serious consequences. it is known in the prior art (see U.S. Pat. Nos. 4,464,179 and 4,291,702) to provide a flush valve assembly to facilitate flushing the line in a blood-pressure monitoring system and to establish a proper drip flow rate of the liquid flow after the flushing action is completed. Flushing devices are used when starting and then maintaining the operation of the blood-pressure monitoring system in which medical personnel must flush the pressure measuring apparatus and the line coupled thereto to eliminate therefrom air or gas bubbles.

Of particular background interest is U.S. Pat. No. 4,934,375 which discloses a complete blood-pressure measuring system in which a saline solution for intravenous infusion is contained in an elevated bag from which it flows through a supply line into the inlet port of a valve, the outlet port of which is coupled by the line to a catheter implanted in a blood vessel in the patient being treated.

Another valve port is coupled by a line to an external pressure sensitive transducer whose electrical signal is conveyed by a cable to a monitor. This monitor displays on its screen the waveform of the signal that represents the varying blood pressure of the patient.

In the arrangement disclosed in U.S. Pat. No. 4,934,375, the components which together create the monitoring system are separated from each other, making it necessary when the system is to be put to use, for medical personnel to then assemble the components. To reduce the need for such an assembly operation, there is disclosed in U.S. Pat. No. 4,545,389 a pressure-responsive sensor incorporated in a unitary assembly with the valve. But other components necessary to the system are not included in this assembly.

In the flush devices for a blood-pressure monitoring system disclosed in U.S. Pat. Nos. 3,675,891 and 4,464,179, there are two separate channels for liquid flow. One is a continuous flow channel and the other a purge or fast flush channel. The continuous flow channel has a small bore that functions as a capillary, whereas the fast flush channel has a substantially larger diameter. Instead of a glass capillary tube to restrict flow, a capillary bore may be laser-drilled in the continuous flow channel.

A conventional system for monitoring blood pressure usually is composed of the following three units which normally are separately manufactured and then intercoupled to create the required assembly:

Unit I. This is a pressure sensing unit in which a pressure-sensitive transducer converts the blood-pressure level of a patient into a corresponding electrical signal which is conveyed to a monitor.

Unit II. This unit includes a fast-flush valve which when actuated effects a fast flush of the system to clear it of deleterious air bubbles. Also included is a flow restrictor to maintain at a slow flow rate the liquid being intravenously infused into the patient's blood stream.

Unit III. This unit includes a stopcock adapted to selectively direct flow to out priming, zeroing and blood sampling operations.

Because units I, II and III are separately manufactured, in order to produce an assembly thereof for installation in a blood-pressure measuring system, these units must be joined together by suitable bonding agents or by UV curable bonds. Not only does his add appreciably to manufacturing costs but it also may result in a defective assembly in that the bonded junctions of the units may crack and not be leak proof.

SUMMARY OF THE INVENTION

In view of the foregoing the main object of this invention is to provide a unitary blood-pressure transducer assembly to be included in a blood-pressure monitoring system, the assembly having a common casing which integrates three sub-assemblies.

More particularly, an object of this invention is to provide a unitary assembly of the above type which integrates a first sub-assembly that includes a pressure sensor, a second sub-assembly that includes a fast-flush valve, and a third sub-assembly that includes a stop cock.

An invasive blood-pressure monitoring system that includes a transducer assembly in accordance with the invention, though not costly or difficult to install, nevertheless makes a significant contribution to the diagnosis of a patient's condition as well as to a treatment appropriate to this condition. A sudden shift in the cardiovascular condition of a patient can be quickly identified by the system and may make possible a prompt, life-saving intervention.

A proper diagnosis of the condition of a patient is aided when the varying blood pressure of the patient is converted into a waveform that is displayed by a monitor. And the system is capable also of monitoring a patient's response to drug therapy to determine whether the dosage being administered to the patient needs to be adjusted to enhance the effectiveness of the therapy.

Among the significant advantages of an assembly in accordance with the invention are the following:

A. The assembly is easy to install, for all that is necessary is to interpose the assembly in the supply line running from an elevated bag containing a saline solution to a catheter implanted in a blood vessel of the patient.

B. The costs of manufacturing the assembly are low as compared to the expenses incurred when the sub-assemblies are separately manufactured and then joined together.

C. Because the unitary assembly is not composed of separate sub-assemblies which are bonded together, the assembly is free of cracks and other defects.

D. The orientation of the adjustable parts of the assembly which must be manipulated by personnel operating the system is such as to facilitate such manipulation.

E. Because the casing of the assembly is molded of transparent plastic material, blood as well as air bubbles which are potentially dangerous, are exposed.

Briefly stated, these objects are attained in a unitary blood-pressure transducer assembly for inclusion in a system adapted to monitor the blood pressure of a patient while the patient is being supplied with a saline or other liquid through a supply line leading to a catheter implanted in a blood vessel. The assembly includes three sub-assemblies housed within a common casing and having an inlet port to be coupled to the upstream section of the line and an outlet port to be coupled to the downstream section thereof whereby the liquid flows through the assembly. Intermediate the ports is a first sub-assembly having a transducer that senses the pressure of a column of liquid developed within the assembly whose pressure varies as a function of the pressure of the blood streaming through the blood vessel.

Adjacent the inlet port is a second sub-assembly that includes a fast-flush valve to purge air bubbles from the assembly and a flow restrictor to maintain liquid flow at a low flow rate. The third sub-assembly which is adjacent the outlet port includes a stopcock to selectively direct flow to allow for priming and zeroing of the system as well as blood sampling.

BRIEF DESCRIPTION OF THE DRAWINGS

For a better understanding of the invention as well as other objects thereof, reference is made to the annexed drawings wherein.

DETAILED DESCRIPTION OF THE INVENTION

Figure 1:
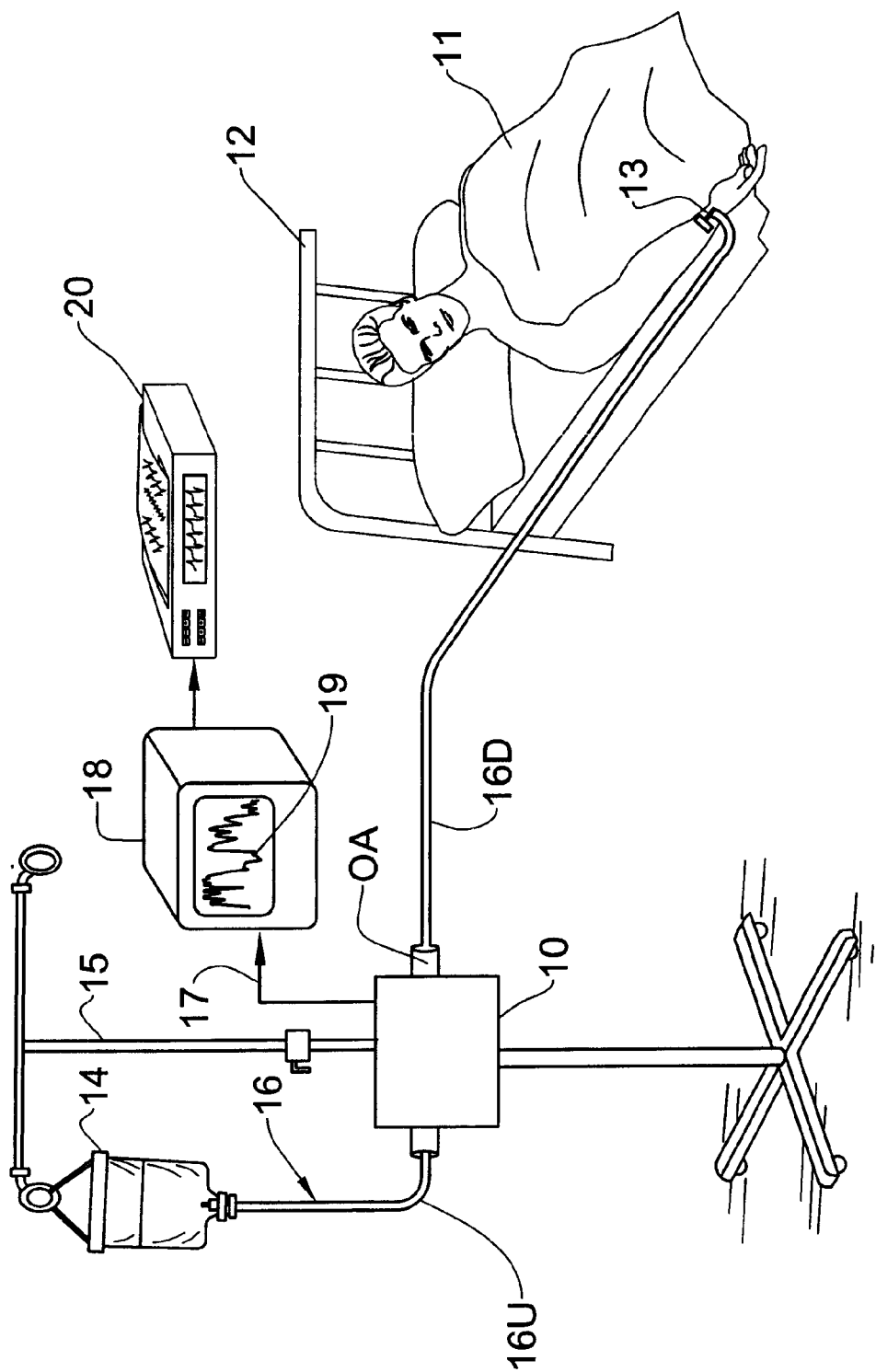
FIG. 1 is a general view of a blood-pressure monitoring system that includes an integrated transducer assembly in accordance with the invention.

The Monitoring System As shown in FIG. 1, an integrated blood-pressure transducer assembly in accordance with the invention is included in a blood-pressure monitoring system in which the pressure to be monitored is that of a patient 11 lying in a hospital bed 12. Implanted in patient 11 is a catheter 13 which invades an artery or vein and therefore communicates with the blood stream An IV liquid source is provided in the form of bag 14 containing a saline solution or other medicinal liquid that is appropriate to the condition of the patient Bag 14 is supported at an elevated position on a vertical pole 15 of adjustable height placed next to the patients' bed. Liquid from the bag flows by gravity through a supply line 16 by way of assembly 10 to catheter 13 which injects the liquid into the blood stream. As a consequence, a column of liquid is developed within the assembly, which column is subjected to the pressure of the blood stream.

Transducer assembly 10 includes in one of its sub-assemblies a pressure transducer such as a piezoelectric element which senses the pressure of the liquid column. The transducer incorporated in assembly 10 yields an electrical signal whose magnitude is proportional to the sensed pressure. This signal is conveyed by cable 17 to an external monitor 18 on whose screen is displaced the waveform of the signal; hence the changing blood pressure of the patient.

In practice, instead of conveying the signal over a cable, the assembly may in its transducer subsection include a miniature, battery powered microwave transmitter module that serves to transmit the transducer signal to a remote monitoring station.

Displayed on the screen 19 of monitor 18 is the waveform of the varying blood-pressure signal. In practice, the screen may be provided with a scale calibrated in units of blood pressure. In this way, a medical attendant can see at a glance the level of the patient's blood pressure and detect any sudden change therein that demands immediate attention.

To provide a permanent record of the patient's varying blood pressure in the course of a hospital stay, the electrical signal from the transducer can also be fed to a print or strip chart recorder 20.

Figure 2:
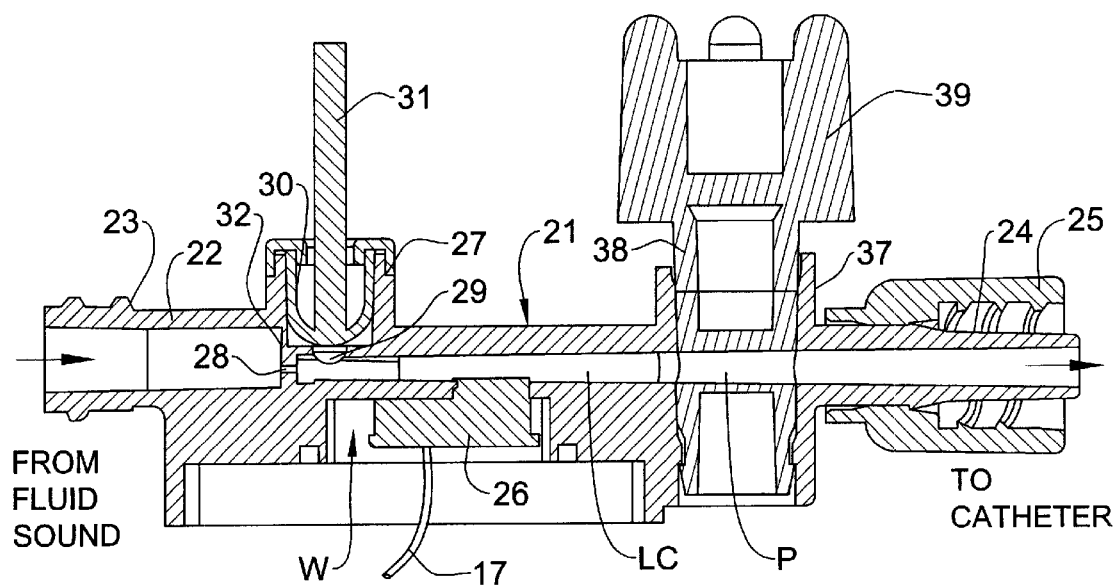
FIG. 2 is a longitudinal section taken through a first embodiment of the assembly.
Figure 3:
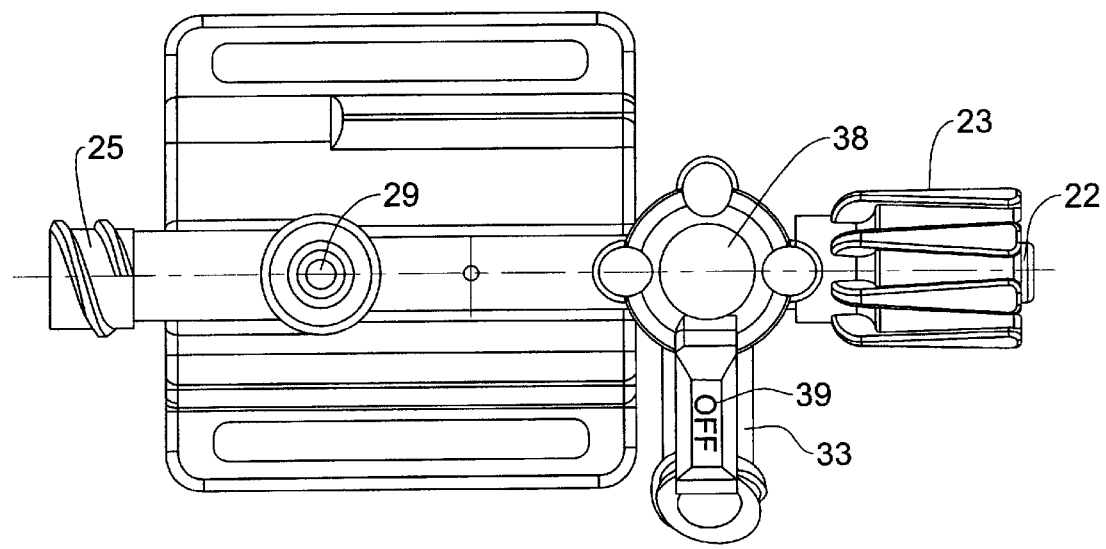
FIG. 3 is a plan view of this assembly.
Figure 4:
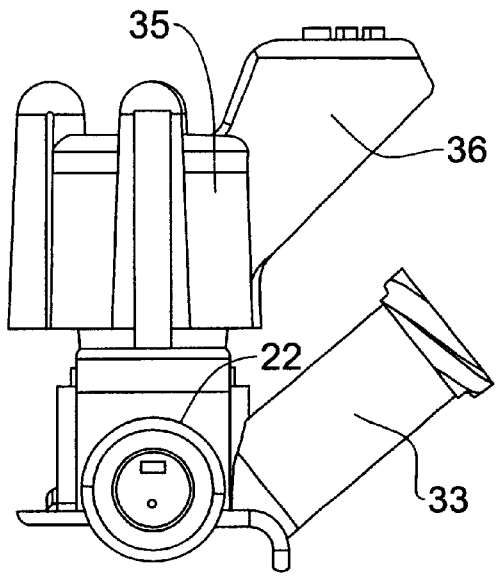
FIG. 4 is an end view of this assembly.

First Embodiment: As illustrated in FIGS. 1, 2 and 3, the tree sub-assemblies which together make up this embodiment of an integrated assembly are housed in a common, generally cylindrical casing 21. Casing 21 is molded of transparent, high-strength plastic material, such as polycarbonate or polypropylene so that medical personnel can observe the flow of liquid within the assembly and the presence of air bubbles.

Projecting from one end of casing 21 in a tubular stub 22 functioning as the inlet port of the assembly, stub 22 being provided with a Luer female coupler 23 for connecting this port to the upstream section 16U of supply line 16 shown in FIG. 1 leading to bag 14 containing a saline or other liquid. Projecting from the other end of casing 21 is a tubular stub 24 functioning as the outlet port provided with a Luer male coupler 25 which is connected to the downstream section 16D of the supply line leading to catheter 13. The assembly therefore acts to modulate the flow of liquid from the source to the patient.

Seated in a well W formed in casing 21 intermediate the inlet and outlet ports is a first sub-assembly that includes a pressure-sensitive traducer 26 which is exposed to the column of liquid LC developed within the assembly. The transducer senses the pressure of the liquid column which depends on the pressure of the blood stream in which the catheter is injected and it generates an electrical signal which is a function of this pressure.

The transducer signal is conveyed by cable 17 to the external monitor 18 in whose screen 19 is displayed the waveform of the signal which reflects variations in the patient's blood pressure. In practice, the screen may be provided with a scale calibrated in units of blood pressure, thereby making it possible for an observer to see at a glance the patient's blood pressure and detect any sudden changes therein that require immediate intervention.

In practice, the assembly can be rendered wireless by including therein a miniature battery-powered microwave transmitter module which conveys the signal to a remote monitor provided with a microwave receiver. In this way, tile monitor can be set up in a hospital at a nurse's station or elsewhere away from the room occupied by the patient.

To provide a permanent record of the patient's blood pressure in the course of a hospital stay, the electrical transducer signal can also be fed to the print or strip chart recorder 20 shown in FIG. 1.

A second sub-assembly which is placed adjacent inlet port 22 of the assembly includes a flush valve 27 whose function is to purge the assembly of air bubbles, and a flow restrictor 28 whose function is to restrict the flow so that it is at a suitably low flow rate to prevent occlusion of the catheter.

Valve 27 is provided with a sealing plug 29 mounted at the apex of a concave, flexible diaphragm 30. The plug normally engages a valve seat to block the flow of liquid into the assembly through an input bore 32 of relatively large diameter. When however sealing plug 29 is raised above the valve seat by its handle 31, the liquid then admitted at a high flow rate flushes out the assembly to remove air bubbles, the flushing liquid being discharged through a stub tube 33 projecting laterally from the casing. In normal operation, liquid passes through the assembly at a slow rate by reason of a capillary bore in flow restrictor 28. This bore may be laser drilled.

Receiving adjacent outlet port 24 of the assembly in a transverse tubular socket 37 projecting at right angles from diametrically-opposed sides of the cylindrical casing is the third sub-assembly consisting of a stopcock 38 having a cylindrical body and a handle 39 extending from its side. The body of this stopcock is provided with a network of tunnels P which at different angular positions of the cylindrical body afford the following:

(a) a flow through passage for the liquid during normal operation of the assembly in which liquid flows at a low flow rate;

(b) a flushing passage in which liquid flows at a fast rate from the inlet port to the lateral port from which it is discharged, and (c) a sampling passage extending between the inlet port and the lateral port Thus the stopcock selectively provided for three modes of operation: normal, flushing and zeroing, and sampling. In FIG. 2, the passage P shown therein which provides a flow-through passage in the assembly illustrates one of these modes.

Figure 5:
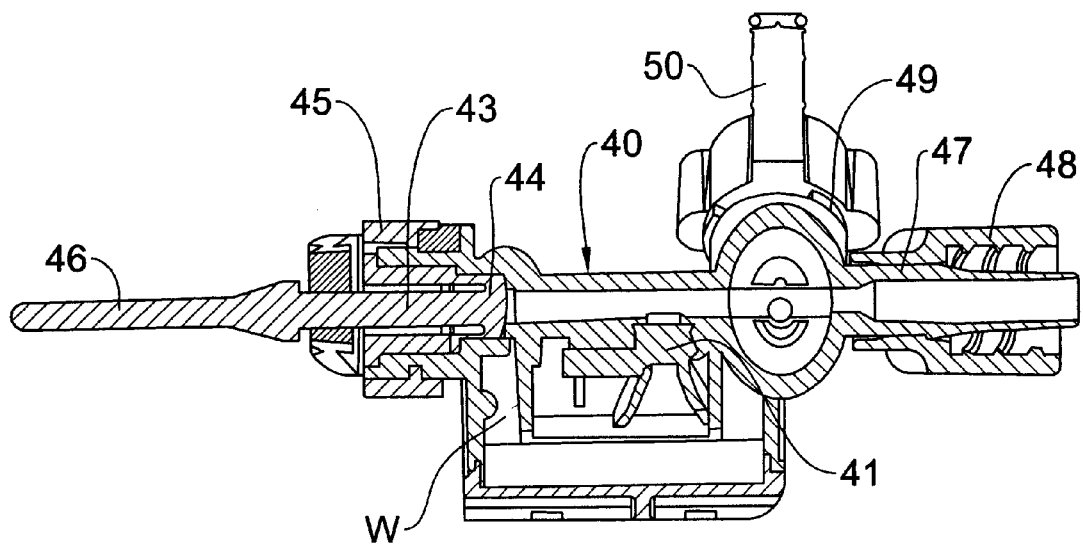
FIG. 5 is a longitudinal section taken through a second embodiment of an assembly in accordance with the invention.
Figure 6:
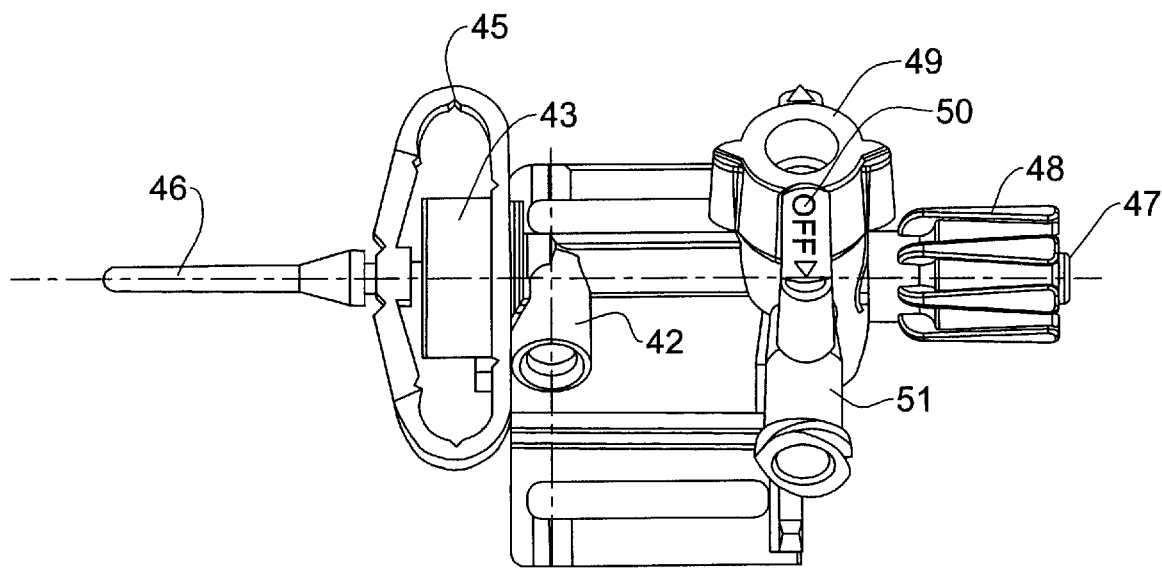
FIG. 6 is a plan view of this assembly.
Figure 7:
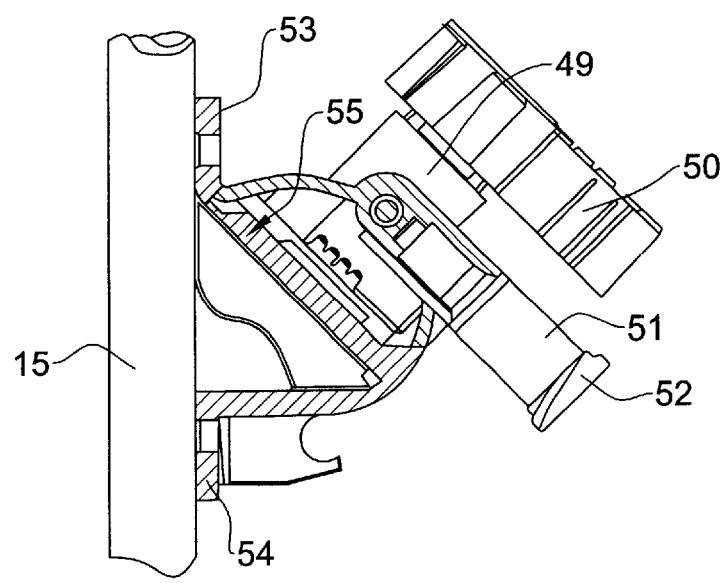
FIG. 7 is an end view thereof

Second Embodiment: In this embodiment illustrated in FIGS. 5, 6 and 7, we again have a unitary assembly of three sub-assemblies housed in a common casing having inlet and outlet ports for interposing the assembly in an IV supply line. However the arrangement of the sub-assemblies with respect to the casing is somewhat different from that shown in the first embodiment In the second embodiment, the cylindrical casing 40 is provided with a well W to accommodate a transducer 41 of the first sub-assembly. This transducer, as in the first embodiment converts the pressure of the liquid column to which it is exposed into an electrical signal which varies as a function of the blood pressure of the patient.

However in the second embodiment its inlet port 42 is not as in the first embodiments coaxial with the outlet port but is formed by a tubular stub projecting laterally from the casing and provided with a Luer coupler.

Associated with inlet port 42 is the second sub-assembly which includes a fast-flush valve 43 whose sealing plug 44 is pressed against a valve seat by a wing-shaped spring 45 coupled to a handle 46. The flush valve is acted by squeezing spring 45 to cause handle 46 to raise plug 44 from the valve seat to admit liquid at a high flow rate into the assembly to flush out air bubbles or one can just pull on the handle to actuate the flush valve.

The third sub-assembly which is adjacent an outlet port 47 provided with a Luer coupler 48 includes a stopcock 49 having a handle 50. Also provided is a fluid discharge tubular stub 51 projecting laterally from the casing adjacent the stopcock, stub 51 terminating in a Luer coupler 52.

The second embodiment operates in the same manner as the first embodiment of the integrated assembly and also combines the three sub-assemblies. And the configuration of its casing is such that it can be injection molded in a single operation, thereby obviating the need to bond together the three sub-assemblies.

However the configuration of the second embodiment is such that when it is directly mounted on a pole or other vertical member adjacent the patient, it is somewhat difficult for an operator to manipulate. We have found that ease of operation is enhanced when the assembly is mounted so that it is inclined with respect to the vertical axis.

To this end, there is provided a mounting fixture 52 having a pair of flat feet 53 and 54 which can be bolted or otherwise attached to the vertical pole in which the IV bag is supported so that the assembly, when mounted on the fixture, will be below the bag to facilitate gravity flow of the liquid through the supply line. But if the IV bag is pressurized, it need not be elevated above the patient.

The assembly is attached to the platform 55 of the fixture which is inclined 45 degrees with respect to the vertical axis of the pole. As a consequence, the stopcock 49 assumes the same angle, making it much easier to manipulate than had it been perpendicular to the pole because the assembly was directly attached thereto.

In the context of a blood-pressure monitoring system, time is of the essence. Should it become necessary to immediately cut off the supply of liquid to the patient or to purge the system of air bubbles to prevent their entry into the blood stream which may have serious consequences, it should not then be necessary for an operator to fumble with the stopcock or with the fast-flush valve. The mounting fixture acts to present to an operator the controls of the assembly so that they can be manipulated without difficulty.

While there has been shown preferred embodiments of a blood-pressure transducer assembly in accordance with the invention, it is to be understood that many changes may be made therein without departing from the spirit of the invention.

What is claimed is:

1. A blood-pressure transducer assembly insertable into a system adapted to monitor the blood pressure of a patient while the patient is being intravenously supplied with a saline or other liquid derived from a source coupled by a supply line to a catheter implanted in the patient, said assembly comprising:

A. a plurality of sub-assemblies housed within a common casing, said casing having an inlet port to be coupled to an upstream section of the supply line, and an outlet port to be coupled to a downs section thereof whereby the liquid flows through the assembly and from there into the blood stream to create within the assembly a column of liquid whose pressure varies as a function of blood pressure, and B. a transducer in one of the sub-assemblies in contact with the column to sense the pressure thereof to produce an electrical signal in accordance with the sensed pressure, said signal being conveyed to an external monitor which displays the waveform thereof.

2. An assembly as in claim 1, in which said inlet port is formed by a tubular stub projecting from the casing and provided with a Luer male coupler.

3. An assembly as in claim 2, in which the outlet port is formed by a tubular stub projecting from the casing and provided with a Luer female coupler.

4. An assembly as set forth in claim 3, in which the outlet and inlet ports lie on a common axis and the transducer lies in a well to make contact with said liquid column which extends along the same axis.

5. An assembly as in claim 1, further including a second sub-assembly adjacent the inlet port provided with a fast flush valve which when actuated permits the liquid to flow through the assembly at a rapid rate to purge the assembly of air bubbles.

6. An assembly as in claim 5, in which the second sub-assembly includes a flow restrictor to permit the liquid to flow through the assembly at a low flow rate.

7. An assembly as set forth in claim 6, in which the flow restrictor is a capillary bore.

8. An assembly as set forth in claim 5, in which the flush valve is provided with a large diameter inlet and a manually-operated sealing plug which normally engages a valve seat to prevent flow into the assembly from the inlet except when the plug is raised above the seat.

9. An assembly as set forth in claim 1, flier including a third sub-assembly adjacent the outlet port provided with a stopcock to selectively direct flow to allow for priming and zeroing of the system as well as for blood sampling.

10. An assembly as in claim 9, further including a mounting fixture for the assembly which when attached to a vertical pole so orients the assembly that the stopcock thereof is at an angle which facilitates its manual operation.

11. An assembly as in claim 10, in which said angle is 45 degrees with respect to a vertical axis.

* * * * *

UNITED STATES PATENT AND TRADEMARK OFFICE
CERTIFICATE OF CORRECTION

PATENT NO. : 6,511,434 B1
DATED : January 28, 2003
INVENTOR(S) : Eyal Haytman et al.

It is certified that error appears in the above-identified patent and that said Letters Patent is hereby corrected as shown below:

<u>Column 6,</u>
Line 67, "downs" should read -- downstream --.

Signed and Sealed this

Sixth Day of May, 2003

JAMES E. ROGAN
*Director of the United States Patent and Trademark Office*